(12) United States Patent
Kim

(10) Patent No.: US 8,784,315 B2
(45) Date of Patent: Jul. 22, 2014

(54) ULTRASOUND SYSTEM FOR CONTROLLING POWER SUPPLIED FROM MULTIPLE POWER SUPPLIES

(75) Inventor: Chil Su Kim, Seoul (KR)

(73) Assignee: Samsung Medison Co., Ltd., Kangwon-Do (KR)

( * ) Notice: Subject to any disclaimer, the term of this patent is extended or adjusted under 35 U.S.C. 154(b) by 98 days.

(21) Appl. No.: 13/331,521

(22) Filed: Dec. 20, 2011

(65) Prior Publication Data

US 2012/0157836 A1    Jun. 21, 2012

(30) Foreign Application Priority Data

Dec. 20, 2010 (KR) .................. 10-2010-0130595

(51) Int. Cl.
*A61B 8/00* (2006.01)
(52) U.S. Cl.
USPC .......................................................... 600/437
(58) Field of Classification Search
USPC ................................ 600/437, 459; 424/9.5
See application file for complete search history.

(56) References Cited

U.S. PATENT DOCUMENTS

| 5,610,509 A | 3/1997 | Nustad |
| 2007/0160540 A1 | 7/2007 | Nishigaki et al. |

FOREIGN PATENT DOCUMENTS

| JP | 2007-175233 | 7/2007 |
| JP | 2008-237280 A | 10/2008 |
| KR | 2010-0084203 A | 7/2010 |

OTHER PUBLICATIONS

European Search Report issued in European Patent Application No. 11193907.0 issued on Apr. 19, 2012.
Korean Office Action issued in Korean Patent Application No. 10-2010-0130595 dated Jun. 19, 2012.
Korean Office Action with English translation issued in Korean Application No. 10-2010-0130595 dated Aug. 28, 2013.
Korean Notice of Allowance with English translation issued in Korean Application No. 10-2010-0130595 dated Nov. 7, 2013.

*Primary Examiner* — Michael Rozanski
(74) *Attorney, Agent, or Firm* — McDermott Will & Emery LLP

(57) ABSTRACT

An ultrasound system, which operates at a plurality of diagnostic modes, includes: an ultrasound probe configured to transmit an ultrasound signal to a target object and receive an ultrasound echo signal reflected from the target object; a power supplying unit configured to supply a power of different voltage levels according to a diagnostic mode to form a transmit pulse signal to be supplied to the ultrasound probe; and a transmitting unit connected to the ultrasound probe and the power supplying unit, the transmitting unit being configured to constantly supply the power in a first voltage level at a transmission time period of an ultrasound signal and vary the voltage level of the power from the first voltage level to a second voltage level based on a predetermined waveform at a transmission idle time period.

1 Claim, 3 Drawing Sheets

ULTRASOUND SYSTEM FOR CONTROLLING POWER SUPPLIED FROM MULTIPLE POWER SUPPLIES

CROSS-REFERENCE TO RELATED APPLICATION

The present application claims priority from Korean Patent Application No. 10-2010-0130595 filed on Dec. 20, 2010, the entire subject matter of which is incorporated herein by reference.

TECHNICAL FIELD

The present invention generally relates to ultrasound systems, and more particularly to an ultrasound system for controlling power supplied from a plurality of power supplies.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional images of internal features of an object (e.g., human organs).

The ultrasound system is configured to transmit an ultrasound signal to a target object and receive an ultrasound signal reflected from the target object (i.e., ultrasound echo signal) to thereby form a receive signal. The ultrasound system is further configured to form an ultrasound image based on the receive signal.

The ultrasound system includes a plurality of power supplies for supplying power of different voltage levels according to diagnostic modes for forming ultrasound images. Conventionally, the ultrasound system includes a transmitter including a plurality of transmit pulsers, which are connected to their respective power supplies, configured to generate transmit pulses according to the diagnostic modes. As such, there is a problem since the size of the ultrasound system and costs are increased.

SUMMARY

An ultrasound system, which operates at a plurality of diagnostic modes, includes: an ultrasound probe configured to transmit an ultrasound signal to a target object and receive an ultrasound echo signal reflected from the target object; a power supplying unit configured to supply a power of different voltage levels according to a diagnostic mode to form a transmit pulse signal to be supplied to the ultrasound probe; and a transmitting unit connected to the ultrasound probe and the power supplying unit, the transmitting unit being configured to constantly supply the power in a first voltage level at a transmission time period of an ultrasound signal and vary the voltage level of the power from the first voltage level to a second voltage level based on a predetermined waveform at a transmission idle time period.

DETAILED DESCRIPTION

Hereinafter, embodiments of the present invention will be described in detail by referring to the accompanying drawings.

Figure 1:
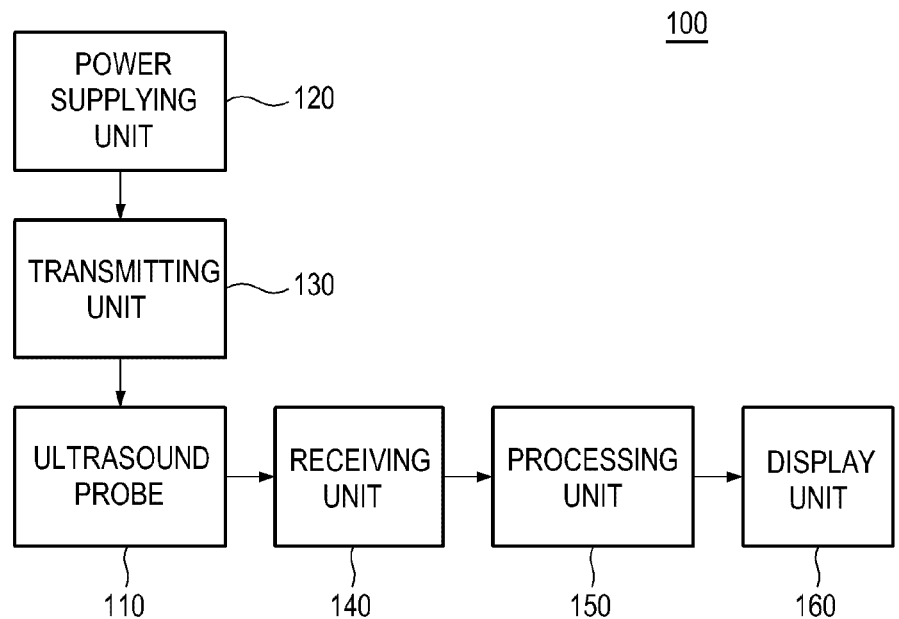
FIG. 1 is a block diagram showing an illustrative embodiment of an ultrasound system.

FIG. 1 is a block diagram showing an illustrative embodiment of an ultrasound system. Referring to FIG. 1, the ultrasound system 100 includes an ultrasound probe 110, a power supplying unit 120, a transmitting unit 130, a receiving unit 140, a processing unit 150 and a display unit 160.

The ultrasound probe 110 includes a plurality of transducer elements (not shown), which are configured to perform reciprocal conversion between an electrical signal and an ultrasound signal. The ultrasound probe 110 is configured to transmit an ultrasound signal to a target object and receive an ultrasound signal reflected from the target object (i.e., ultrasound echo signal) to thereby output an electrical receive signal. The receive signal may be an analog signal. The ultrasound probe 110 may include a curved probe, a linear probe and the like.

The power supplying unit 120 is configured to supply powers having a plurality of voltage levels, which are necessary for generating transmit pulse signals according to a plurality of diagnostic modes of the ultrasound system 100. The transmit pulse signals are provided to the ultrasound probe 110. In one embodiment, the power supplying unit 120 includes a plurality of power supplies, which are operable to supply powers of a plurality of different voltage levels to obtain ultrasound images corresponding to the plurality of diagnostic modes. The ultrasound images may include a brightness mode (B-mode) image, a continuous wave Doppler image, a spectral Doppler image, a color Doppler image, a 3-dimensional image, an elastic image and the like. In one embodiment, the power supplying unit 120 may include a first power supply, which is operable to supply a first power of a first voltage level (e.g., 80V) to obtain a first ultrasound image (e.g., B-mode image, 3-dimensional image or elastic image) and a second power supply operable to supply a second power of a second voltage level (e.g., 60V) to obtain a second ultrasound image (e.g., color Doppler image or pulse Doppler image).

Although the embodiment has been described above that the power supplying unit 120 includes two power supplies 121 and 122, the number of the power supplies may not be limited thereto. The number of the power supplies and the voltage levels of the respective powers may be variable according to necessity.

The transmitting unit 130 is configured to generate the transmit pulse signal to obtain an ultrasound image by considering the transducer elements and a focal point, and to provide it to the ultrasound probe 110. Also, the transmitting unit 130 is configured to control an operation of the power supplying unit 120.

Figure 2:
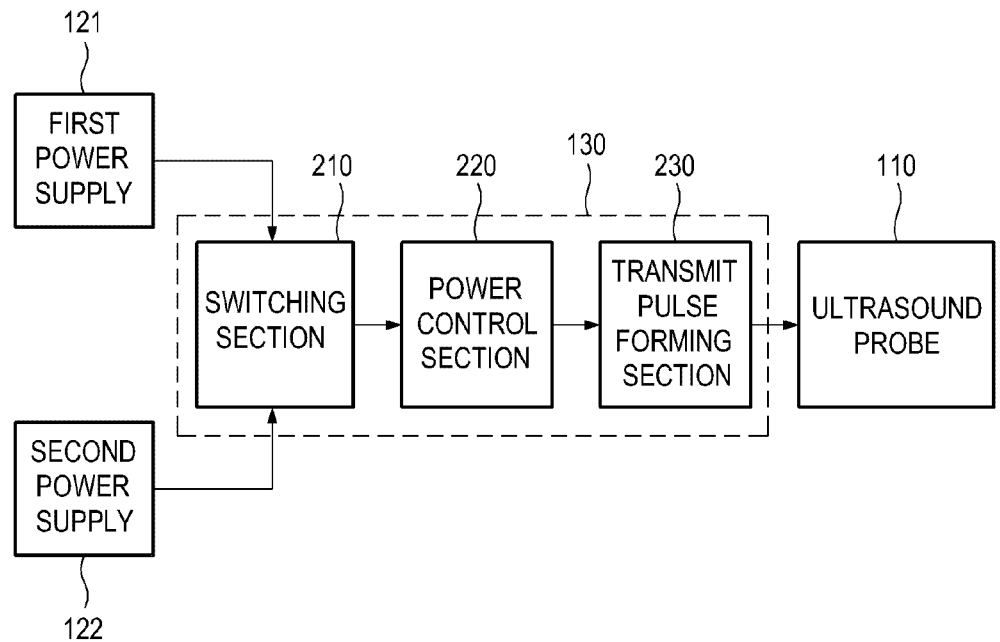
FIG. 2 is a block diagram showing an illustrative embodiment of a transmitting unit.

FIG. 2 is a block diagram showing an illustrative embodiment of the transmitting unit 130. Referring to FIG. 2, the transmitting unit 130 may include a switching section 210, a power control section 220 and a transmit pulse forming section 230.

The switching section 210 is configured to perform switching operable to select one of the power supplies in the power supplying unit 120 according to a selected diagnostic mode. That is, the switching section 210 is operable to transfer one of the powers, which are provided from the plurality of power supplies in the power supplying unit 120, to the power control section 220 according to the selected diagnostic mode. In one embodiment, the switching section 210 includes a switch (now shown), which is operable to connect one of the power supplies to the power control section 220 and a switch controller (not shown) operable to control an operation of the switch.

A pulse wave ultrasound system may operate at two time periods of a transmission period of an ultrasound signal and a reception period of an ultrasound echo signal. That is, the transmission period of the ultrasound signal is a reception idle period at which the ultrasound echo signal is not received, while the reception period of the ultrasound echo signal is a transmission idle period at which the ultrasound signal is not transmitted. The power control section 220 is configured to operate such that the power supplied from the power supplying unit 120 is supplied in a constant voltage level. In one embodiment, if a power corresponding to a next transmission period, which is determined according to a next diagnostic mode, is supplied through the switching section 210 from the power supplying unit 120 in the transmission idle period, then the power control section 220 is operable to increase or decrease a voltage level of the power, which is supplied to the transmit pulse forming section 230, to a voltage level of the power supplied from the power supplying unit 120 along a predetermined waveform.

The transmit pulse forming section 230 is configured to form transmit pulse signals to acquire ultrasound images by using the powers supplied from the power control section 220. The transmit pulse forming section 230 may includes a plurality of transmit pulsers (not shown) and a transmit pulser drive (not shown).

Hereinafter, an operation of the transmitting unit 130 will be described in detail by referring to the accompanying drawings.

Figure 3:
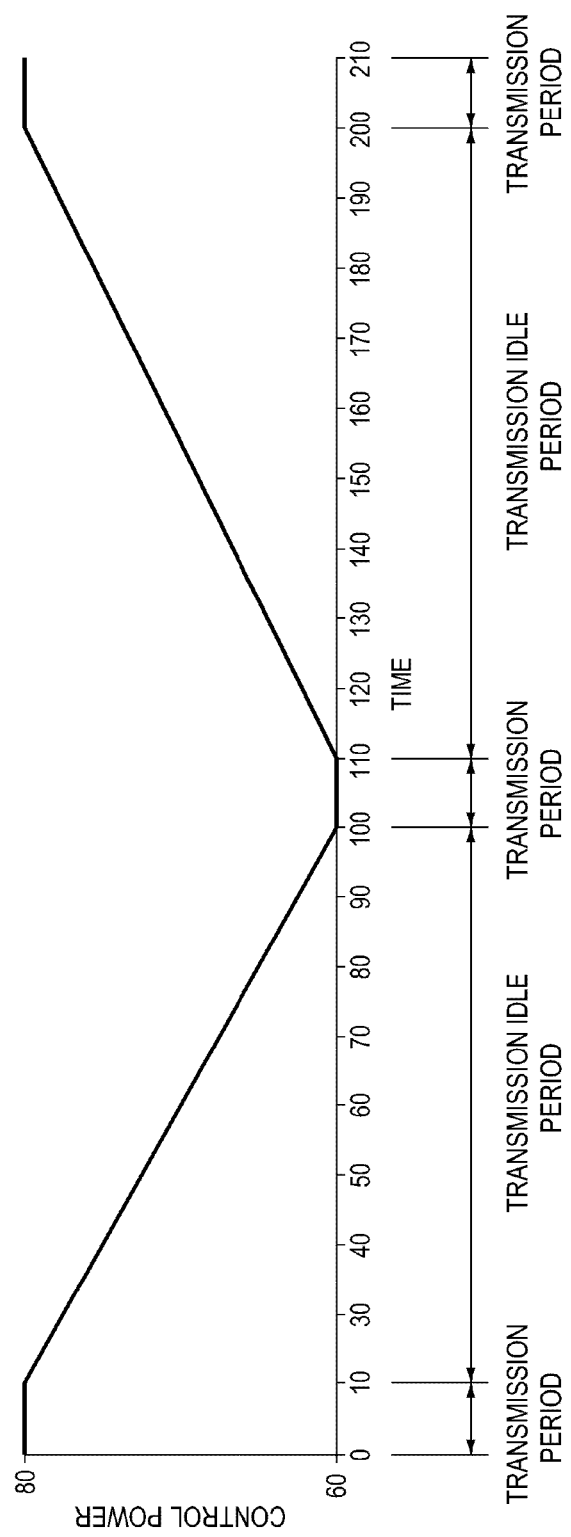
FIG. 3 is an exemplary diagram showing an example of a predetermined waveform.

In one embodiment, it will be described that the diagnostic mode is a BC dual mode, which operates to provide a B mode image and a color flow Doppler image at the same time. As shown in FIG. 3, if a first power (e.g., 80V) is supplied from the first power supply 121 in a transmission period of an ultrasound signal (time period between 1 to 10), then the power control section 220 is configured to supply the first power to the transmit pulse forming section 230 in a constant voltage level. Thus, the transmission pulse forming section 230 may form a first transmit pulse signal to acquire a B-mode image by using the first power, which is supplied in a constant voltage level from the power control section 220.

Subsequently, the power control section 220 is configured to gradually decrease the voltage level of the first power to a voltage level corresponding to a next transmission period in a transmission idle period (time period between 10 to 100) based on a predetermined waveform having a predetermined slope. Thus, occurrence of a noise due to the supply of the power whose voltage level is steeply changed may be prevented.

Thereafter, as shown in FIG. 3, if a second power (e.g., 60V) is supplied from the second power supply 121 in a transmission period of an ultrasound signal (time period between 100 to 110), then the power control section 220 is configured to supply the second power to the transmit pulse forming section 230 in a constant voltage level. Thus, the transmission pulse forming section 230 may form a second transmit pulse signal to acquire a color Doppler image by using the second power, which is supplied in a constant voltage level from the power control section 220.

Subsequently, the power control section 220 is configured to gradually increase the voltage level of the second power to a voltage level corresponding to a next transmission period in a transmission idle period (time period between 110 to 200) based on a predetermined waveform having a predetermined slope. Thus, occurrence of a noise due to the supply of the power whose voltage level is steeply changed may be prevented.

Figure 4:
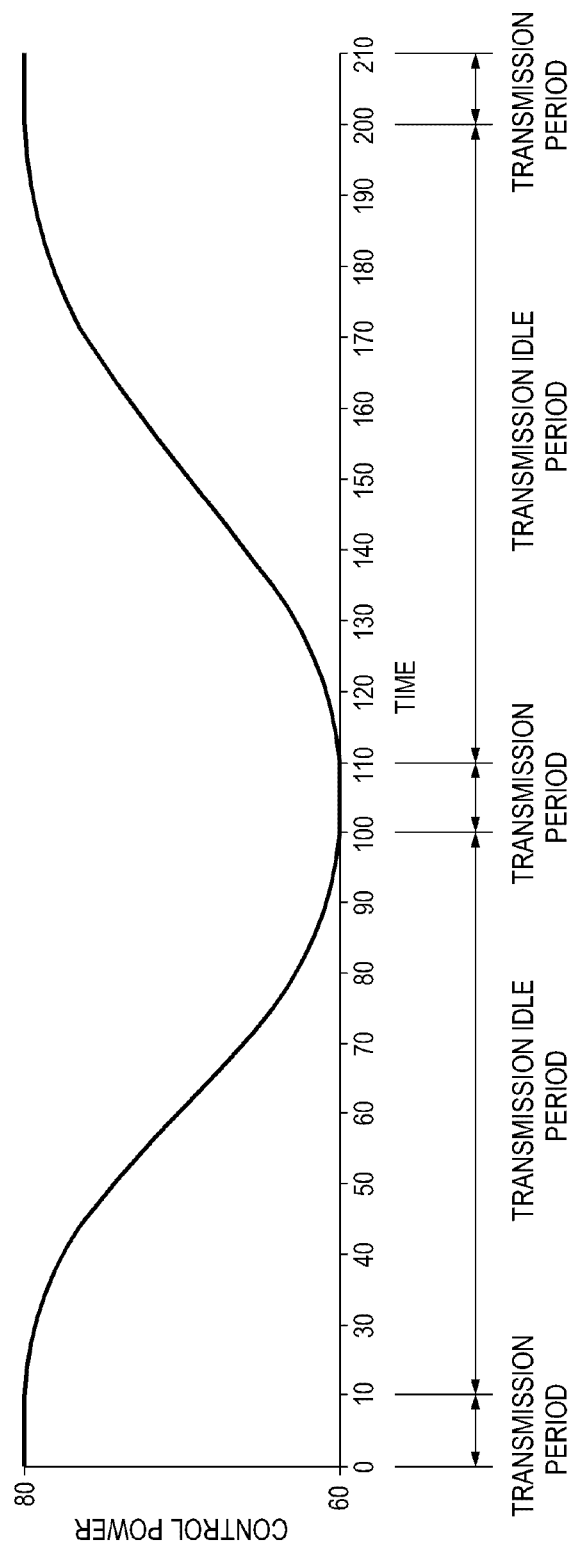
FIG. 4 is an exemplary diagram showing another example of a predetermined waveform.

In another embodiment, as shown in FIG. 4, if a first power (e.g., 80V) is supplied from the first power supply 121 in a transmission period of an ultrasound signal (time period 1 to 10), then the power control section 220 is configured to supply the first power to the transmit pulse forming section 230 in a constant voltage level. Thus, the transmission pulse forming section 230 may form a first transmit pulse signal to acquire a B-mode image by using the first power, which is supplied in a constant voltage level from the power control section 220.

Subsequently, the power control section 220 is configured to gradually decrease the voltage level of the first power to a voltage level corresponding to a next transmission time period in a transmission idle period (time period 10 to 100) based on a predetermined waveform, e.g., cosine waveform. Thus, occurrence of a noise due to the supply of the power whose voltage level is steeply changed may be prevented.

Thereafter, as shown in FIG. 4, if a second power (e.g., 60V) is supplied from the second power supply 121 in a transmission period of an ultrasound signal (time period 100 to 110), then the power control section 220 is configured to supply the second power to the transmit pulse forming section 230 in a constant voltage level. Thus, the transmission pulse forming section 230 may form a second transmit pulse signal to acquire a color Doppler image by using the second power, which is supplied in a constant voltage level from the power control section 220.

Subsequently, the power control section 220 is configured to gradually increase the voltage level of the second power to a voltage level corresponding to a next transmission period in a transmission idle time period (time period 110 to 200) based on a predetermined waveform, e.g., cosine waveform. Thus, occurrence of a noise due to the supply of the power whose voltage level is steeply changed may be prevented.

Although the embodiments have been described in that the diagnostic mode is the BC dual mode, it may not be limited thereto. It should be understood to a person skilled in the art that the diagnostic mode may be changed according to necessity.

Referring back to FIG. 1, the receiving unit 140 is configured to perform analog-to-digital conversion on the receive signal outputted from the ultrasound probe 110 to thereby output a digital signal. Also, the receiving unit 140 is further configured to perform receive-focusing upon the signal by considering the transducer elements and a focal point to form a receive-focused signal.

The processing unit 150 is configured to form ultrasound data corresponding to the ultrasound image based on the receive-focused signal provided from the receiving unit 140. The ultrasound data may include radio frequency data or in-phase/quadrature data. However, the ultrasound data may not be limited thereto. The ultrasound image may be formed through scan conversion or rendering.

The display unit 160 is configured to display the ultrasound image formed in the processing unit 150. The display unit 160 may include a cathode ray tube, a liquid crystal display, an organic light emitting diodes and the like.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system operating at a plurality of diagnostic modes, comprising:
   an ultrasound probe configured to transmit an ultrasound signal to a target object during a transmission period and receive an ultrasound echo signal reflected from the target object during a transmission idle period;
   a power supplying unit comprising a plurality of power supplies configured to supply a power of different voltage levels according to a diagnostic mode to form a transmit pulse signal to be supplied to the ultrasound probe;
   a switching section configured to connect one of the plurality of power supplies; and
   a power control section, at the transmission period, configured to uniformly supply a first power of a first voltage level supplied from a first power supply of the plurality of power supplies connected to the switching section, and at the transmission idle period after the switching section is connected to a second power supply which supplies a second power of a second voltage level, configured to increase or decrease the voltage level of the power supplied by the power control section from the first voltage level to the second voltage level based on a predetermined cosine waveform.

* * * * *